United States Patent [19]

Klyosov et al.

[11] Patent Number: 5,961,941

[45] Date of Patent: *Oct. 5, 1999

[54] PRODUCTION OF PRECIPITATED CALCIUM CARBONATE FROM PAPERMAKING SLUDGE AND SLUDGE-DERIVED ASH

[75] Inventors: Anatole A. Klyosov, Newton; George P. Philippidis, Boston; Yiannis A. Monovoukas, Waltham, all of Mass.

[73] Assignee: Thermo FiberGen, Inc., Bedford, Mass.

[*] Notice: This patent is subject to a terminal disclaimer.

[21] Appl. No.: 08/955,167

[22] Filed: Oct. 21, 1997

Related U.S. Application Data

[63] Continuation-in-part of application No. 08/877,548, Jun. 17, 1997.

[51] Int. Cl.⁶ ........................................... C01F 1/00
[52] U.S. Cl. ............................. 423/165; 423/155
[58] Field of Search .................... 423/155, 162, 423/158, 163, 430, 165; 210/928; 162/189

[56] References Cited

U.S. PATENT DOCUMENTS

| | | | |
|---|---|---|---|
| 3,812,235 | 5/1974 | Robinson | 423/158 |
| 3,833,463 | 9/1974 | Croom | 210/928 X |
| 4,018,877 | 4/1977 | Woode | 423/432 |
| 4,100,264 | 7/1978 | Heytmeijer et al. | 423/430 |
| 4,124,688 | 11/1978 | Shibazaki et al. | 423/432 |
| 4,133,894 | 1/1979 | Shibazi et al. | 423/432 |
| 4,157,379 | 6/1979 | Arika et al. | 423/430 |
| 4,367,207 | 1/1983 | Vanderheiden | 423/432 |
| 4,420,369 | 12/1983 | Eaton et al. | 210/928 X |
| 4,714,603 | 12/1987 | Vanderheiden | 423/432 |
| 5,007,964 | 4/1991 | Tsukisaka et al. | 106/464 |
| 5,075,093 | 12/1991 | Tanaka et al. | 423/432 |
| 5,120,521 | 6/1992 | Ebinuma et al. | 423/432 |
| 5,164,172 | 11/1992 | Katayama et al. | 423/432 |
| 5,232,678 | 8/1993 | Bleakley et al. | 423/432 |
| 5,292,495 | 3/1994 | Nakajama et al. | 423/432 |
| 5,342,600 | 8/1994 | Bleakley et al. | 423/432 |
| 5,376,343 | 12/1994 | Fouche | 423/165 |
| 5,558,850 | 9/1996 | Bleakley et al. | 423/432 |

*Primary Examiner*—Steven Bos
*Assistant Examiner*—Stuart L. Hendrickson
*Attorney, Agent, or Firm*—Cesari and McKenna, LLP

[57] ABSTRACT

Extraction of calcium salts from papermaking sludge or sludge-derived ash is accomplished by mixing with a solution of an inorganic or organic acid. The acid extraction typically results in solubilization of other salts as well, e.g., those of aluminum, magnesium and iron. However, because these non-calcium salts precipitate as hydroxides at lower pH than calcium hydroxide, a caustic (or any other alkaline agent, in a solid or liquid form) is gradually added to precipitate non-calcium salts to facilitate their removal from solution (generally by filtration or centrifugation) prior to precipitation of calcium hydroxide. The desired calcium salt is then precipitated through addition of the appropriate acid anion (either by way of the acid or a salt having greater water solubility than the resulting calcium salt).

13 Claims, No Drawings

PRODUCTION OF PRECIPITATED CALCIUM CARBONATE FROM PAPERMAKING SLUDGE AND SLUDGE-DERIVED ASH

RELATED APPLICATION

This application is a continuation-in-part of allowed application Ser. No. 08/877,548, filed Jun. 17, 1997.

FIELD OF THE INVENTION

The present invention relates to utilization of renewable resources and industrial wastes, such as pulp and paper sludge and products of their incineration, and in particular to recovery of purified calcium carbonate from these materials.

BACKGROUND OF THE INVENTION

Pulp and paper sludge (a byproduct of primary pulping operations, recycle streams or waste paper pulping and the like), as well as the products of its incineration, represent an environmental and disposal problem for manufacturers of pulp and paper. Generally, pulp and paper sludge is unsuitable for paper making, although it generally contains the same components—cellulose, lignin, hemicellulose, calcium carbonate, clay, and other inorganic components—as those present in the paper pulp itself.

Paper sludge has traditionally been disposed of by landfilling, composting, incorporation into cement, and incineration. The latter option, in turn, creates another problem, namely, disposal of the resulting ash, which often makes up to 50% (and sometimes as much as 80% or higher) of the volume of the sludge itself. Calcium carbonate, in the form of precipitated calcium carbonate (PCC) or ground calcium carbonate (GCC), typically constitutes 20% and up to 75% of dry sludge content. Calcium carbonate is a natural carbonate which is loaded, typically together with clay, into paper as a coating and filler to improve the mechanical characteristics as well as the appearance of paper. Despite their natural abundance, calcium salts are generally expensive products because of the difficulties and expenses of their purification from natural mineral deposits. For instance, paper-quality PCC is typically produced from natural limestone via extensive processing including the calcination of limestone in an industrial kiln (to produce either a calcitic or a dolomitic lime), slaking, slurrying, carbonating, and a number of refining steps.

Unfortunately, the inorganic content of sludge and sludge-derived ash is generally largely or totally wasted. At best, the prior art describes utilization of incineration ash for production of low-end, impure products of limited market value. For example, Sohara ("Recycling Mineral Fillers from Deinking Sludges," *Paper Recycling '96 Conf.* 1996) details processing of such ash to precipitate calcium carbonate on the surface of the ash itself, which acts merely as nucleation center. In particular, an aqueous slurry of incineration ash is carbonated with carbon dioxide gas; calcium carbonate nucleates on the ash and grows during the precipitation reaction. The resulting mixture of precipitated calcium carbonate and ash still contains from 10% to 30% incineration ash, and represents an undifferentiated agglomeration of minerals and clay.

Nor does the prior art provide an effective way of isolating calcium salts from a mixture that includes salts of other cations, as, for example, from solubilized minerals from papermaking sludge. While various techniques for precipitating $CaCO_3$ from aqueous suspensions of calcium hydroxide are known (see, e.g., U.S. Pat. Nos. 4,018,877, 4,124,688, 4,133,894, 4,157,379, 4,367,207, 4,714,603, 5,075,093, 5,120,521, 5,164,172, 5,232,678, 5,342,600, and 5,558,850), these are of limited usefulness in separating calcium from other salts.

Accordingly, lacking in the prior art is a cost-effective method of producing pure, high-grade calcium carbonate from papermaking sludge or ash derived therefrom.

DESCRIPTION OF THE INVENTION

Summary of the Invention

The invention provides a method of obtaining relatively pure calcium carbonate (up to 97–99%) from papermaking sludge (pressed or dried) or incinerated sludge (ash) notwithstanding the various chemical changes that occur during incineration. Preferably, the invention is applied to a mixture of mineral salts obtained from sludge (e.g., in accordance with the '548 application), although the approach described herein is applicable to many mixtures of salts regardless of their origin.

Papermaking sludge typically contains a rather high amount of $CaCO_3$ (up to 20%–50% of solids or more). In the presence of many acids, $CaCO_3$ is solubilized as a result of conversion into the acid-anion salt in the reaction mixture. Since papermaking sludge often contains an organic fraction (cellulose, lignin, hemicellulose), some organic materials, pentose sugars in particular, can be extracted by acids as well, thereby decreasing the purity of the target calcium salt. Also, $CaCO_3$ in the sludge is typically accompanied by aluminosilicates (clay) and other minerals (as pigments, fillers, etc.), such as those based on magnesium, potassium and others. These can be partially extracted with acids as well. Obviously, the extent of acid extraction/solubilization of the inorganic and organic components, making the target calcium salt less pure, greatly depends on conditions of the sludge treatment with acids, nature of the acid, the acid concentration, and contact time with the acid in particular.

In accordance with the '548 application, pressed or dried sludge or sludge-derived ash is combined with a dilute acid, following which the solid content is separated from the liquid content to obtain a solids-free solution of calcium and other salts. The separation of the liquid from the solid residue may be carried out using belt presses, screw presses, centrifuges, filters, other suitable means of separation, or a combination of means. With regard to sludge, this may be mixed with a solution of an inorganic or organic acid—generally 0.1% to 55% by weight, preferably 2% to 20%, and most preferably 3% to 16% by weight; the optimal concentration depends on process conditions (in particular, calcium carbonate content in the processed papermaking sludge) and the desirable concentration of the target salt in the solution produced. In preferred embodiments, the mixture is combined with 2% to 20%, and most preferably 3% to 6% HCl; 2% to 52%, and most preferably 6% to 8%, $HNO_3$; 2% to 30%, and most preferably 8% to 16%, acetic acid. Generally, the amount of acid added into the reaction mixture preferably is 0.8 to 2.0 times the stoichiometric calcium carbonate content in the mixture, more preferably 0.8 to 1.2 times the stoichiometric content, and most preferably matched to the stoichiometric content of calcium carbonate in the mixture. The acid-containing mixture is incubated (with agitation, if desired, to shorten the reaction time) to solubilize the desired minerals, following which the liquid phase is isolated, and mineral salts recovered therefrom.

With regard to ash, this material is mixed with a solution of an inorganic or organic acid—generally 2% to 35% by weight, preferably 5% to 25%, and most preferably 8% to 20% by weight; the optimal concentration depends on process conditions (in particular, calcium carbonate content in the ash) and the desirable concentration of the target salt in the solution produced. In preferred embodiments, the mixture is combined with 8% to 14% HCl; 5% to 20%, and most preferably 8% to 17%, $HNO_3$; 5% to 21%, and most preferably 10% to 15%, acetic acid. Generally, the amount of acid added into the reaction mixture preferably is 0.8 to 2.0 times the stoichiometric calcium carbonate content in the mixture, more preferably 0.8 to 1.2 times the stoichiometric content, and most preferably matched to the stoichiometric content of calcium carbonate in the mixture. Once again, the acid-containing mixture is incubated (with agitation, if desired, to shorten the reaction time) to solubilize the desired minerals, following which the liquid phase is isolated, and mineral salts recovered therefrom.

After completion of calcium solubilization, which can be verified by determination of the calcium concentration or content in the bulk solution, calcium is present in solution with the salts of other cations. As noted earlier, $CaCO_3$ in sludge is typically accompanied by aluminosilicates salts based on magnesium, potassium, iron and other cations. These salts may be partially extracted with acid as well, rendering the desired calcium salt less pure. In particular, when the extract is carbonated, the accompanying salts precipitate as a dirty, colored, bulky sediment.

The present invention exploits the differential solubility properties of the various salts typically in solution following dilute-acid extraction. In a first aspect, the invention comprises a technique for purifying calcium from a mixed mineral-salt mixture, or "cocktail." In preferred embodiments, a solution of relatively pure calcium carbonate is obtained from the mineral-salt cocktail (e.g., the sludge or ash extract). However, as detailed below, it is also possible to obtain pure solutions of other calcium salts having limited, pH-dependent aqueous solubilities.

In particular, it is found that aluminum, magnesium and iron salts solubilized along with calcium by acid extraction of sludge precipitate as hydroxides at lower pH than calcium hydroxide. For example, the pK (negative logarithm of dissociation constants) is 9.7 for $Al(OH)_2^+$ in aqueous solution at 25° C., 8.3 for $Al(OH)_3$, 2.6 for $MgOH^+$, but is 1.2 for $CaOH^+$. These values indicate that half the amounts of these elements in water solutions convert to their respective hydroxides and precipitate (as aluminum hydroxide and aluminum oxide, magnesium hydroxide, and various other, minor hydroxides and oxides) at distinct pH levels: for aluminum salts at pH 4.3 and 5.7, respectively; for magnesium salts at pH 11.4; and for calcium salts at pH 12.8. Indeed, precipitation of calcium hydroxide does not even begin as a practical matter until pH 11.7, when a fine suspension is observed.

In preferred embodiments, a caustic (or any other alkaline agent, in a solid or liquid form) is gradually added to precipitate non-calcium salts as their hydroxides, which are removed from solution (generally by filtration or centrifugation) prior to precipitation of calcium hydroxide. For some extracts (typically for calcium chlorides and nitrates, having a greenish color at pH 1.7–3.0) a dirty, gray-colored bulky precipitate starts forming at pH 4, and continues to form through pH 7 and above; slightly more of the precipitate is typically observed up to pH 10 and through to pH 11.7 (the onset of calcium hydroxide precipitation). For some extracts (typically for those containing calcium acetate, and having a reddish, brownish, or greenish color at pH 4.5–5.2, depending on the sludge utilized) a partial decolorization is observed along with a bulky precipitate forming at pH 8–9, and which continues to form through p11 (at which pH the extract is still slightly colored) to pH 11.6–11.7 (at which pH the extract often is decolorized and all light-colored precipitate is sedimented). Calcium salts remain stable in solutions at those pH values (i.e., calcium hydroxide is not formed in appreciable quantities and, hence, is not precipitated below pH 11.7). Therefore, the purification technique of the invention can be stopped at any suitable acidity level above pH 4.4, preferably at or above pH 7, and most preferably at pH above 10, particularly at pH 11.5–11.7. At pH 11.7 calcium hydroxide may begin to form a little of a white cloudiness in the extract, but it would typically constitute only a very small fraction of calcium present in the solution.

In a second aspect, the invention provides for precipitation of a calcium salt (e.g., $CaCO_3$) from the purified calcium solution obtained as described above. That is, after separation and removal of the non-calcium salts, a clear solution of a calcium salt typically remains. A target calcium salt, insoluble under these or modified conditions, is obtained through addition of the appropriate acid anion (either by way of the acid or a salt having greater water solubility than the resulting calcium salt). Thus, for example, carbonation of the calcium solution results in precipitation of a relatively pure white calcium carbonate. This precipitation may be accomplished using water-soluble carbonates or bicarbonates (such as $K_2CO_3$, $Na_2CO_3$, soda ash, etc.), or by carbonation of the water solution with carbon dioxide, or by any other suitable carbonation method. Using different carbonation methods (e.g., at different temperatures), different concentrations of water-soluble calcium salts, different carbon-dioxide flow rates, etc., different morphological forms of calcium carbonate may be produced as precipitates for use in the many known applications of calcium carbonate.

Other calcium salts that may be precipitated in accordance with this aspect of the invention include calcium borate, calcium cinnamate, calcium citrate, calcium fumarate, calcium gluconate, calcium lactate, calcium malate, calcium oxalate, calcium salicylate, calcium succinate, calcium sulfate, calcium sulfite, calcium benzoate, and calcium arsenate. These are precipitated using a water-soluble salt of the anion, or, if the target calcium salt precipitates at lower pH, the anion acid (or a combination of the acid with a salt of the anion). For example, sulfuric acid may be added to the calcium solution to precipitate calcium sulfate.

In a variation to the above approach, it has been found that carbonation can be used to accomplish both purification and precipitation of calcium carbonate. The carbonation increases the pH and also forces precipitation of the less soluble carbonate salts of cations other than calcium. Generally, after a dirty, colored precipitate is formed, and the extract is largely clarified (i.e., changed from a brownish or dirty-greenish to a clear solution), carbonation is stopped, and the dirty precipitate separated by filtration, centrifugation, or other suitable means. Further carbonation results in a white precipitate of pure calcium carbonate.

The calcium salt obtained in the purified and decolorized liquid can be employed in solution, in a concentrated form, or in the solid state (e.g., by evaporation of the water phase) as a separate product. Using the approach of the present invention, it is possible to obtain solutions of purified calcium salts from a number of papermaking sludge materials, as well as their incineration ash preparations obtained at various thermal conditions.

Detailed Description of the Preferred Embodiments

EXPERIMENTAL PROCEDURES

1. Determination of Calcium

TAPPI procedure T 247 cm-83 (Classical Method—1983) was used for calcium determination in sludge and pulp. The procedure is based on EDTA titration of $HNO_3$-soluble calcium in ashed sludge and pulp. EDTA forms a highly-colored water-soluble complex with calcium, while other metal ions present are masked with triethanolamine. The ash was placed in 10 mL of Milli-Q and 3 mL of 5 M nitric acid (325 mL of concentrated nitric acid diluted to 1 L with water) was added. The mixture was heated for 5–10 min on a steam bath, transferred into a 300-mL flask, the volume was adjusted to 100 mL, 5 mL of 8 M KOH solution was added, the flask was shaken occasionally for 5 min, and 5 mL of triethanolamine (diluted 10 times), and then 2 mL of hydroxylamine hydrochloride solution (2 g/100 mL) were added, along with 100 mg of cal-red indicator. The mixture was titrated with 0.02 M EDTA solution to a color change from red-wine to blue. Calcium content (in %) was calculated as EDTA(mL)×0.08016/g of dry weight ash.

2. Determination of Solids and Calcium Content in Acid Calcium Extracts, Dried at 105° C. and Combusted at 525° C.

Weight determination of compounds dissolved in acid water extracts, described below as "solids," was performed by evaporation of a 5- or 10-mL sample at 105° C.—until a constant a weight was attained—using the Mettler Infrared Moisture Analyzer, or a programmable oven.

Salts of calcium and other metals, typically present in acid extracts of papermaking sludge, often contain chemically bound water. Since this water often remains bound at 105° C., the concentration of calcium (as well as other metals) is typically "diluted" when determined in the dried extracts.

Examples of such calcium salts include: $CaCl_2.H_2O$, $CaCl_2.2H_2O$ (loses both water molecules at 200° C.), calcium chloride aluminate $3CaO.Al_2O_3.CaCl_2.10H_2O$ (loses 1 water molecule at 105° C. and 8 water molecules at 350° C.), $Ca(NO_3)_2.3H_2O$, $Ca(NO_3)_2.4H_2O$ (loses water at 132° C.), $Ca(CH_3COO)_2.2H_2O$ (loses 1 water molecule at 84° C.), $Ca(CH_3COO)_2.H_2O$ (loses the water molecule at about 150° C., converts into $CaCO_3$ at 160° C.), $CaCO_3.6H_2O$. If not taken into consideration, these bound water molecules affect analytical results. Some other bound water-containing compounds that might easily get into the sludge acid-extracted solids and their carbonated precipitates, and therefore affect analytical data, are $Mg(CH_3COO)_2.4H_2O$, $Mg(CO_3).3H_2O$, $Mg(CO_3).5H_2O$, and others.

To eliminate the bound water as much as possible without substantially altering the principal chemical composition of the solids, the solids were dried at 105° C., analyzed, and then combusted at 525° C. Reduction in weight as a result of the combustion was typically ascribed either to a combination of organic materials and bound water (when whole sludge extracts were analyzed), or to bound water alone (when extracts of the ashed sludge were analyzed). Calcium acetate on heating above 160° C. decomposes to $CaCO_3$ and acetone. Therefore, calcium content in the combusted solids, extracted with acetic acid, can be indicative of the purity of the originally solubilized calcium acetate. For example, if elemental calcium content in the combusted solids is 40% by weight (corresponding to pure $CaCO_3$), the acetic acid calcium extract contains practically pure calcium acetate.

Calcium in the acid extracts dried at 105° C. and 525° C. was determined using TAPPI procedure T 247 cm-83, as described above. Calcium in liquid acid extracts was determined in 1-mL or 3-mL aliquots also processed according to said TAPPI procedure.

Solubilization of calcium is further described in the following Examples 1–24, purification of calcium salt extracts from accompanying salts—in Examples 25–50, and precipitation and characterization of calcium carbonate—in Examples 35–44 and 51–66.

The following Examples 1–24, performed generally in accordance with the teachings of the '548 application, detail isolation of the mixed-salt cocktail from sludge and sludge-derived ash.

EXAMPLE 1

This example describes solubilization of calcium (in the form of calcium chloride) from mixed office sludge by diluted hydrochloric acid, in a proportion of 1.1 times the stoichiometric amount of calcium carbonate content in the sludge. The initial sludge material had a moisture content of 50.2%, an ash content of 37.0% (dry matter), and an elemental calcium content of 8.6%, representing a calcium carbonate content of 21.5% in the whole dried sludge. Moisture content was determined either by heating the material in a temperature-programmed furnace at 105° C. to constant weight, typically overnight, or using a Mettler Moisture Analyzer. Ash content was determined by combustion of the material overnight in a furnace at 525° C.

The solubilization was performed as follows. 1,800 mL (2,124 g) of 37.2% hydrochloric acid was diluted to 18.22 L with water, and the resulting 3.7% (v/v) or 4.3% (w/w) HCl was added to 9.11 kg of the wet sludge (taking into account water content in the sludge, the final concentration of HCl in the liquid was 2.9% v/v, or 3.4% w/w). That amount of hydrochloric acid was 11% higher compared with the stoichiometric amount needed for complete solubilization of the calcium carbonate present in the sludge. The mixture was incubated for 1 hr at room temperature with a moderate agitation. Supernatant was then decanted, the solid residue pressed, and 14 L of liquid collected. The pH of the liquid was 1.7. The liquid contained 5.5% solids, as shown by evaporation of a 5-mL sample at 105° C.

Elemental calcium content in the liquid extract was 14.2 mg/mL, translating into 3.9% $CaCl_2$, or 70.9% $CaCl_2$ content in the total solids extracted from the sludge.

EXAMPLE 2

The procedure of Example 1 was repeated, but with the difference that the amount of hydrochloric acid added to the sludge was 1.3 times the stoichiometric calcium carbonate content in the sludge. 2,523 mL (2,977 g) of 37.2% HCl was diluted to 24 L with water, and the resulting 3.9% (v/v) or 4.5% (w/w) HCl was added to 11 kg of the wet sludge (taking into account water content in the sludge, the final concentration of HCl in the liquid was 3.2% v/v, or 3.7% w/w). 22 L of extract was collected, the pH of which was 1.1. The liquid contained 6.4% solids (dried at 105° C.). Elemental calcium content in the liquid extract was 13.8 mg/mL, translating into 3.8% $CaCl_2$, or 59% $CaCl_2$ content in the total solids, extracted from the sludge.

EXAMPLE 3

The procedure of Example 1 was repeated, but with the difference that the amount of hydrochloric acid added to the sludge was stoichiomctric with respect to the calcium carbonate content in the sludge. 151 mL (178.2 g) of 37.2% HCl was diluted to 1.5 L with water, and the resulting 3.7% (v/v) or 4.3% (w/w) HCl was added to 830.5 g of the wet sludge (taking into account water content in the sludge, the final concentration of HCl in the liquid was 2.9% v/v, or 3.4% w/w). 1.7 L of extract was collected, the pH of which was 2.3. The liquid contained 4.9% solids (dried at 105° C.). Elemental calcium content in the liquid extract was 12.2 mg/mL, translating into 3.4% $CaCl_2$, or 69% $CaCl_2$ content in the total solids extracted from the sludge.

EXAMPLE 4

The procedure of Example 1 was repeated, but with the difference that the amount of HCl added to the sludge was the 1.2 times the stoichiometric calcium carbonate content in the sludge. 2,357 mL (2,781 g) of 37.2% HCl was diluted to 24 L with water, and the resulting 3.65% (v/v) or 4.2% (w/w) HCl was added to 11 kg of the wet sludge (taking into account water content in the sludge, the final concentration of HCl in the liquid was 3.0% v/v, or 3.5% w/w). 19 L of extract was collected, the pH of which was 2.2. The liquid contained 5.5% solids (dried at 105° C.). Elemental calcium content in the dried solids was 29.5%, translating into 81.9% $CaCl_2$ content in the total solids extracted from the sludge.

All 19 L of the extract collected were passed through a 0.45-micron membrane. 10 L of a greenish liquid were collected. Elemental calcium content in the filtered liquid was 16.2 mg/mL, translating into 4.5% $CaCl_2$ in the liquid.

EXAMPLE 5

The procedure of Example 1 was repeated, but with a different sample of mixed office sludge, and with a different amount of hydrochloric acid (in a proportion of 2.05 times the stoichiometric calcium carbonate content in the sludge). The sludge material had a moisture content of 43.4%, an ash content of 32.7% (per dry matter), and an elemental calcium content of 9.2%, representing a calcium carbonate content of 23% in the whole dried sludge.

82 mL of 20% (v/v) or 23.8% (w/w) HCl was first diluted with 82 mL of water, and then the resulting 10% (v/v) HCl was added to 100 g of the wet sludge. The final concentration of HCl in the reaction mixture was 7.9% (v/v) or 9.1% (w/w). After overnight incubation the supernatant was decanted, and the collected insoluble sludge residue placed into a Buchner funnel and subjected to vacuum filtration using house vacuum. 132 mL total of the liquid was collected and filtered through Whatman No. 1 filter paper. Solids content in the collected liquid was 12.0%, as shown by evaporation of a 10-mL sample at 105° C. Combustion of the dried solids at 525° C. reduced their weight by 43.5% (the theoretical value for transition of $CaCl_2.2H_2O$ into $CaCl_2$ is 24.5%).

EXAMPLE 6

This example describes solubilization of calcium (in the form of calcium chloride) from yet another mixed office sludge, combusted under controlled conditions at 525° C. The dry ash contained 24.9% elemental calcium, translating into 62.3% calcium carbonate. The solubilization was performed by diluted HCl, in amount of 1.3 times the stoichiometric proportion of calcium carbonate.

The solubilization was performed as follows. 500 mL of 11.9% (w/w) of HCl, prepared by diluting 535 mL (636.65 g) of 37.4% HCl to 2 L, was added to 100 g of the dry ash. That amount of HCl was 31% higher than the stoichiometric amount needed for complete solubilization of the calcium carbonate present in the ash. The mixture was agitated and left overnight at room temperature. Supernatant was then separated from the solid residue by decanting and filtering, and 243 mL of liquid was collected. The liquid contained 15.8% solids, as was shown by evaporation of a 10-ml sample at 105° C. The elemental calcium content in the dried solids was 27.6%, translating into 77% CaCl, or 101% $CaCl_2.2H_2O$.

Combustion of the dried solids at 525° C. reduced their weight by 24.7% (the theoretical value for transition of $CaCl_2.2H_2O$ into $CaCl_2$ is 24.5%), and the elemental calcium content in the combusted solids was 29%, translating into 80% $CaCl_2$ in the total solids.

EXAMPLE 7

The procedure of Example 6 was repeated, but with the difference that the ash, treated with dilute HCl, was obtained by combustion at 900° C. The dry ash contained 30.0±0.4% elemental calcium, translating into 42.0±0.6% calcium oxide equivalent. The amount of HCl used for the solubilization was 1.1 times the stoichiometric proportion of calcium carbonate in the ash.

The solubilization was performed as follows. 170 mL of 11.9% (w/w) HCl, prepared as described in Example 6, was added to 34 g of the dry ash. That amount of HCl was 9% higher than the stoichiometric amount needed for complete solubilization of calcium carbonate present in the ash. The mixture was agitated and left overnight at room temperature. Supernatant was then separated from the solid residue by decanting and filtering, and 72 mL of liquid was collected. The liquid contained 18.8% solids, as shown by evaporation of a 10-mL sample at 105° C. Elemental calcium content in the dried solids was 27.4%, translating into 76% CaCl, or 100% $CaCl_2.2H_2O$.

Combustion of the dried solids at 525° C. reduced their weight by 25.5% (the theoretical value for transition of $CaCl_2.2H_2O$ into $CaCl_2$ is 24.5%), and the elemental calcium content in the combusted solids was 32.3%, translating into 90% $CaCl_2$ in the total solids.

EXAMPLE 8

The procedure of Example 1 was repeated, but with the difference that dilute nitric acid was used for solubilization of calcium (in the form of calcium nitrate) from mixed office sludge from the same source as in Example 1, and of a similar composition, and that the amount of nitric acid added to the sludge was stoichiometric with respect to the calcium carbonate content in the sludge.

1,740 mL (2,453 g) of 69.8% nitric acid was diluted to 24 L with water, and the resulting 5.1% (v/v) or 6.9% (w/w) $HNO_3$ was mixed with 11.2 kg of the wet sludge (taking into account water content in the sludge, the final concentration of $HNO_3$ in the liquid was 4.2% v/v, or 5.8% w/w). That amount of nitric acid was equal to the stoichiometric amount needed for complete solubilization of the calcium carbonate present in the sludge. The mixture was incubated for 1 hr at room temperature with a moderate agitation. Supernatant was then decanted, the solid residue pressed, and 20 L of liquid was collected. The pH of the extract was 1.9. The liquid contained 7.7% solids, as shown by evaporation of a 5-mL sample at 105° C.

Elemental calcium content in the liquid extract was 13.7 mg/mL, translating into 5.6% $Ca(NO_3)_2$, or 73% $Ca(NO_3)_2$ content in the total solids, extracted from the sludge.

EXAMPLE 9

The procedure of Example 8 was repeated, but with the difference that the amount of $HNO_3$ added to the sludge was the 0.9 times the stoichiometric proportion of calcium carbonate in the sludge.

1,650 mL (2,327 g) of 69.8% nitric acid was diluted to 24 L with water, and the resulting 4.8% (v/v) or 6.6% (w/w) $HNO_3$ was mixed with 12 kg of the wet sludge (taking into account water content in the sludge, the final concentration of $HNO_3$ in the liquid was 3.8% v/v, or 5.3% w/w). The mixture was incubated for 1 hr at room temperature with a moderate agitation. Supernatant was then decanted, the solid residue pressed, and 20 L of liquid was collected. The pH of the extract was 1.6. The liquid contained 6.8% solids, as was shown by evaporation of a 5-mL sample at 105° C.

Elemental calcium content in the liquid extract was 15.36 mg/mL, translating into 6.3% $Ca(NO_3)_2$, or 93% $Ca(NO_3)_2$ content in the total solids, extracted from the sludge.

EXAMPLE 10

The procedure of Example 8 was repeated, but a different sample of mixed office sludge was treated with dilute nitric acid, in an amount stoichiometric with respect to the calcium carbonate in the sludge. The calcium carbonate content in the dry sludge was 29.3%, and the moisture content 63.9%.

680 mL (956 g) of 69.8% nitric acid was diluted to 1 L with water, and the resulting 47.5% (v/v) or 52.3% (w/w) $HNO_3$ was mixed with 5 kg of the wet sludge (taking into account water content in the sludge, the final concentration of $HNO_3$ in the liquid was 11.3% v/v, or 14.9% w/w). The mixture was incubated for 3 hr at room temperature without agitation. Supernatant was then decanted, the solid residue pressed, and 980 mL of liquid was collected. The pH of the extract was 3.3. The liquid contained 17.9% solids, as shown by evaporation of a 5-mL sample at 105° C.

Elemental calcium content in the dried extract was 22.9%, translating into 93.9% $Ca(NO_3)_2$ content in the total solids, extracted from the sludge.

EXAMPLES 11 AND 12

The procedure of Example 8 was repeated, but with the difference that dilute nitric acid was used for solubilization of calcium (in the form of calcium nitrate) from the ash obtained by combustion of the mixed office sludge at 525° C.

(EXAMPLE 11) 200 g of the ash was mixed with 1.8 L of 20% nitric acid (143 mL of 69.9% nitric acid diluted to 500 mL with water). That amount of nitric acid corresponded to 2.3 times the stoichiometric proportion of calcium carbonate in the ash. The slurry was agitated and left overnight at room temperature. The liquid collected was of a gel-like appearance and contained 18.5% solids, as shown by evaporation of a 10-mL sample at 105° C. The elemental calcium content in the dried solids was 13.75±0.05% (based on two independent measurements), translating into 56.4% $Ca(NO_3)_2$, or 81.2% $Ca(NO_3)_2.4H_2O$.

(EXAMPLE 12) In a similar experiment, 200 g of the ash was mixed with 3.0 L of 20% nitric acid, prepared as in Example 11. That amount of nitric acid corresponded to 3.8 times the stoichiometric proportion of calcium carbonate in the ash. The slurry was agitated and left overnight at room temperature. The liquid collected contained 11.0±0.1% solids (based on two separate measurements), as was shown by evaporation of a 10-mL sample at 105° C. The elemental calcium content in the dried solids was 13.6±0.1% (based on two independent measurements), translating into 55.8% $Ca(NO_3)_2$, or 80.3% $Ca(NO_3)_2.4H_2O$.

Combustion of the dried solids from both experiments at 525° C. reduced their weight by 64% (the theoretical value for the transition of $Ca(NO_3)_2.4H_2O$ into anhydrous calcium carbonate is 57.6%). The calcium content in the combusted solids was determined to be 38.4%, corresponding to calcium carbonate of 96% purity.

EXAMPLE 13

The procedure of Example 1 was repeated, but with the difference that dilute acetic acid was used for solubilization of calcium (in the form of calcium acetate) from mixed office sludge from the same source as in Example 1, and that the amount of acetic acid added to the sludge was stoichiometric with respect to calcium carbonate in the sludge.

1,371 mL (1,440 g) of glacial acetic acid was diluted to 10 L with water, and the resulting 13.7% (v/v) or 14.3% (w/w) acetic acid was mixed with 10 kg of the wet sludge (taking into account water content in the sludge, the final concentration of acetic acid in the liquid was 9.2% v/v, or 9.6% w/w). The mixture was incubated for 3 hr at room temperature with a moderate agitation. Supernatant was then decanted, the solid residue pressed, and 6.5 L of liquid was collected. The pH of the extract was 5.5. The liquid contained 9.6% solids, as shown by evaporation of a 5-mL sample at 105° C.

Elemental calcium content in the liquid extract was 20.2 mg/mL, translating into 8.0% calcium acetate, or 83% calcium acetate content in the total solids, extracted from the sludge.

EXAMPLE 14

The procedure of Example 13 was repeated, but a different sample of mixed office sludge was treated with a stoichiometric amount of acetic acid. The calcium carbonate content in the dry sludge was 21.1%, and the moisture content 46.6%.

644 mL (676 g) of glacial acetic acid was diluted to 5.93 L with water, and the resulting 10.85% (v/v) or 11.3% (w/w) acetic acid was mixed with 5.0 kg of the wet sludge (taking into account water content in the sludge, the final concentration of acetic acid in the liquid was 7.8% v/v, or 8.1% w/w). The mixture was incubated for 4 hr at room temperature with a moderate agitation. Supernatant was then decanted, the solid residue pressed, and 5 L of liquid was collected. The pH of the extract was 5.2.

After 45 min of reaction, the elemental calcium content in a sample of the washed and dried solid residue was 2.0% (5% calcium carbonate); after 4 hours, the solid residue contained 0.5% elemental calcium, translating into 1.25% calcium carbonate.

Solids content in the obtained extract was 9.2%, as shown by evaporation of a 5-mL sample at 105° C. The elemental calcium content in the solids was 22.3%, translating into 88.1% calcium acetate anhydrous. Elemental calcium content in the liquid extract was 17.0 mg/mL, translating into 6.7% calcium acetate.

EXAMPLES 15 AND 16

The procedure of Example 13 was repeated, but with a different sample of mixed office sludge, and with the difference that the amount of acetic acid added to the sludge was the 2.6 times the stoichiometric amount of calcium carbonate content in the sludge. The sludge material was dried, dust-free, and had a moisture content of 3.9%, an ash content of 60%, and an elemental calcium content of 5.4%, resulting in a calcium carbonate content of 13.5% in the whole dried sludge.

(EXAMPLE 15) 300 g of the dried sludge was added by portions of 80–120 g into 625 mL of 20% (v/v) acetic acid (prepared by mixing 125 mL of glacial acetic acid and 500 mL of tap water) at room temperature. A moderate evolution of carbon dioxide was observed. The mixture was left overnight, following which supernatant was decanted, and 310 mL of the brownish liquid was then collected. The solids content was 15.7%, as was shown by evaporation of a 10-mL sample at 105° C. The elemental calcium content in the liquid was 28.25 mg/mL, translating into 11.2% calcium acetate.

(EXAMPLE 16) 3.84 kg of the dried sludge was added by batches of 100–200 g into 8 L of 20% (v/v) acetic acid (prepared by mixing of 1.6 L of glacial acetic acid and 6.4 L of tap water). After overnight incubation the supernatant was decanted, and the collected insoluble sludge residue placed into a large Buchner funnel and subjected to vacuum filtration using house vacuum. 3.9 1 of the liquid, pH 4.4, was collected. The liquid was filtered through Whatman No. 1 filter paper, resulting in a brownish clear solution with solids content of 15.4% (shown by evaporation of a 10-mL sample at 105° C.). The calcium content in the liquid was 23.0 mg/mL, translating into 9.1% calcium acetate.

EXAMPLES 17 AND 18

The procedure of Examples 11 and 12 was repeated, but with the difference that dilute acetic acid was used for solubilization of calcium (in the form of calcium acetate) from the ash obtained by combustion of the mixed office sludge at 525° C.

(EXAMPLE 17) 200 g of the ash was mixed with 1.8 L of 20% (v/v) or 21% (w/w) acetic acid. That amount of acetic acid corresponded to 2.5 times the stoichiometric proportion of calcium carbonate in the ash. The slurry was agitated and left overnight at room temperature. The liquid collected contained 14.0% solids, as shown by evaporation of a 10-mL sample at 105° C. The theoretical amount of calcium acetate, formed in the reaction mixture, would have been 10.9% solids. The elemental calcium content in the dried extract was determined to be 19.6±0.8% (based on four independent measurements), translating into 77% $Ca(CH_3COO)_2$, or 86% $Ca(CH_3COO)_2.H_2O$.

(EXAMPLE 18) In a similar experiment, 200 g of the ash was mixed with 3.0 L of 20% (v/v) or 21% (w/w) acetic acid. That amount of acetic acid corresponded to 4.2 times the stoichiometric proportion of calcium carbonate in the ash. The slurry was agitated and left overnight at room temperature. 2.7 L of liquid was collected. The liquid collected contained 9.2±0.2% solids (based on two separate measurements), as was shown by evaporation of a 10-mL sample at 105° C. The theoretical amount of calcium acetate formed in the reaction mixture would have been 6.6% by weight. The elemental calcium content in the dried extract was determined to be 19.2±0.4% (based on two independent measurements), translating into 76% $Ca(CH_3COO)_2$, or 85% $Ca(CH_3COO)_2.H_2O$.

Combustion of the dried solids from both experiments at 525° C. reduced their weight by 53% (the theoretical value for the transition of $Ca(CH_3COO)_2.H_2O$ into anhydrous calcium carbonate is 43.2%, since calcium acetate loses a water molecule and an acetone molecule in the conversion to calcium carbonate). The calcium content in the combusted solids was determined to be 39.2%, corresponding to 98% calcium carbonate (the theoretical calcium content is 40%). Since the initial ash did not contain organic matter, the last figure indicates that the acetic acid extract contained calcium acetate of 98% purity.

EXAMPLES 19 THROUGH 21

These examples describe and compare the solubilization of calcium (in the form of calcium chloride, calcium nitrate or calcium acetate) from an industrial incineration ash. The moisture content in the ash was 32.3%. The dried ash contained 16.5% elemental calcium, translating into 23.1% calcium oxide equivalent.

The solubilization was performed by diluted hydrochloric, nitric, and acetic acids, in amounts close to the stoichiometric equivalent of the calcium oxide in the ash. 100 g of dry incineration ash was treated with the following acid solutions:

(Example 19) 300 mL of 7.3% (v/v) or 8.4% (w/w) HCl, prepared by diluting of 225 mL (265.5 g) of 37.4% HCl to 500 mL with water, resulting in 16.8% (v/v) or 18.4% (w/w) HCl, and by a further mixing of 130 mL of the diluted acid with 170 mL of water;

(Example 20) 400 mL of 13% (v/v) or 17% (w/w) nitric acid, prepared by diluting of 143 mL (201.6 g) of 69.9% nitric acid to 500 mL with water, resulting in 20% (v/v) or 25.2% (w/w) $HNO_3$, and by a further mixing of 260 mL of the diluted nitric acid with 140 mL of water; and (Example 21) 400 mL of 12.5% (v/v) or 13.1% (w/w) acetic acid, prepared by diluting of 125 mL (131.25 g) of glacial acetic acid to 625 mL with water, resulting in 20% (v/v) or 20.8% (w/w) acetic acid, and by a further mixing of 250 mL of the diluted acetic acid with 150 mL of water.

In all the three examples the amounts of the acids were close to stoichiometric equivalents: 3% excess of the acid, no excess, and 6% excess, respectively. The amount of extract recovered was 200 mL (Example 19), 210 mL (Example 20), and 270 mL (Example 21). The theoretical amount of solids (as anhydrous salts) in the extracts were: 15.3% for $CaCl_2$, 16.9% for $Ca(NO_3)_2$, and 16.3% for $Ca(CH_3COO)_2$.

Table 1 shows the amount of solids extracted from the ash after the liquids collected were dried at 105° C.

TABLE 1

Concentration of solids extracted from an industrial incineration ash. 100 g of ash was treated with approximately stoichiometric amounts of hydrochloric, nitric, and acetic acids.

| Acid | Solids concentration in the extracts, dried at 105° C. % | Ca content in solids, dried at 105° C., % | Weight loss of solids at 525 °C., % | Ca content in combusted solids, % |
|---|---|---|---|---|
| Hydrochloric | 11.9 ± 1.3 | 25.2 | 21.5 | 33.1 |
| Nitric | 23.7 ± 0.5 | 21.7 | 52.4 | 40.3 |
| Acetic | 10.5 ± 1.1 | 25.7 | 46.7 | 36.1 |

It is apparent that acid-extracted chlorides, nitrates, and acetates, dried at 105° C., contained a high fraction of components volatile at 525° C. and/or decomposed at that temperature. In the case of calcium chloride, combustion apparently eliminates bound water. Calcium nitrate converts to practically pure calcium carbonate (the theoretical calcium content is 40%, compared to 40.3% in Table 1). Calcium acetate loses a water molecule and an acetone molecule (the theoretical weight loss is 42.3%, see Example 18) and converts to calcium carbonate (the theoretical calcium content is 40%, compared to 36.1% in Table 1, and corresponds to $CaCO_3$ of 90.3% purity).

EXAMPLES 22 THROUGH 24

The procedure of Examples 19 through 21 was repeated for the same industrial incineration ash and for the same experimental conditions.

(Example 22) After treatment with hydrochloric acid 260 mL of the extract was obtained (pH 2.9, elemental calcium concentration 19.3 mg/mL), corresponding to 5.4% calcium chloride by weight.

(Example 23) After treatment with nitric acid, 350 mL of the extract was obtained (pH–0.2, elemental calcium concentration 26.9 mg/mL), corresponding to 11.0% calcium nitrate by weight.

(Example 24) After treatment with acetic acid, 325 mL of the extract was obtained (pH 3.8, elemental calcium content 10.8 mg/mL), corresponding to 4.3% calcium acetate by weight. The color of the filtered clear extract was distinctly orange.

The following Examples 25–50 detail purification of calcium salt extracts from accompanying salts with or without precipitation of calcium carbonate.

EXAMPLE 25

This example describes purification of a calcium chloride solution obtained by processing of mixed office sludge in accordance with Example 1. Non-calcium salts, also extracted from the sludge, were eliminated by raising the pH of the solution (in this particular case, using sodium hydroxide) and by removing the precipitated accompanying salts as their insoluble hydroxides.

Three 400-mL batches of the extract obtained in Example 1 by treatment of the mixed office sludge with dilute hydrochloric acid (in a proportion of 1.1 times the stoichiometric amount) were used in this Example. The pH of the solution was 1.7, and the solution contained 5.5% (w/w) soluble material, 70.9% of which was calcium chloride. The last figure was calculated from elemental calcium content in the liquid extract equal to 14.2 mg/mL, translating into 3.9% $CaCl_2$ in the extract by weight.

50% NaOH was added dropwise to each of the batches of the extract. When the pH reached 4.0–4.1, the color of the liquid changed from greenish to gray, and a dark-gray precipitate appeared. The calcium content in the supernatant did not change, and was equal to 14.2 mg/mL. The precipitate in the first batch was collected. Increasing the pH to 7.0 in the second batch with 50% NaOH, and then with 4% NaOH, produced light-gray bulky precipitate, whereas the calcium content in the supernatant remained unchanged. The precipitate in the second batch was collected at this point. Further increase of the pH to 11.4 in the third batch with 4% NaOH produced a very light-colored (almost white) bulky precipitate, and resulted in clear, practically colorless solution with the calcium content reduced only slightly to 13.7 mg/mL (translating into a calcium chloride concentration in the extract of 3.8%, compared to the initial 3.9%). The precipitate in the third batch was collected, and the clear supernatant separated. Further increase in the pH of the supernatant to 11.5 and then to 11.7–11.8 resulted in some turbidity consisting of fine white particles, apparently calcium carbonate. Calcium content in the filtered supernatant at these pH values decreased to 13.5 mg/mL and 12.2 mg/mL, respectively.

The collected precipitates were dried at 105° C., and analyzed for some metals (see Table 10 below). Of 22 g of solids, contained in 400 mL of the extract and including 15.6 g calcium chloride (5.5% total solids, and 3.9% calcium chloride by weight, see above), 183 mg precipitated (as hydroxides) at pH 4.0–4.1, 905 mg at pH 7.0, and 2.035 g at pH 11.4. The resulting practically colorless solution of calcium chloride (supplemented with sodium hydroxide and sodium chloride, formed in situ) was used for calcium carbonate precipitation (see Examples 51 and 52).

EXAMPLES 26 AND 27

The procedure of Example 25 for calcium chloride purification was repeated, but with the difference that calcium chloride solutions were obtained pursuant to Examples 2 and 3, using HCl in stoichiometric proportions of 1.3 and 1.0, respectively.

(EXAMPLE 26) 400 mL of the liquid extract was taken, pH 1.1. The extract contained 6.4% solids (59% that was calcium chloride), 13.8 mg/mL elemental calcium, 3.8% $CaCl_2$ by weight. Through the addition of 50% NaOH, the pH was raised to 6.9. A bulky, gray precipitate appeared. The filtered supernatant had an elemental calcium content of 13.2 mg/mL. Adding the same 50% NaOH solution to the supernatant, the pH was increased to 11.5. The precipitate was separated, and the calcium concentration of the supernatant was 12.2 mg/mL. Further increase of the pH to 11.7 led to minor precipitation of white particles. The liquid had a calcium content of 11.9 mg/mL. The filtered supernatant was used for calcium carbonate precipitation (see Example 53).

(EXAMPLE 27) 1.7 L of the liquid extract was taken, pH 2.3, 4.9% solids (69% that was calcium chloride), 12.2 mg/mL elemental calcium, 3.4% $CaCl_2$ by weight. Through the addition of 50% NaOH, the pH was raised to 8.5. A bulky, gray precipitate appeared. The filtered supernatant has the same calcium content, i.e., 12.2 mg/mL. Increasing the pH to 10.7 only slightly changed the calcium content, to 11.4 mg/mL. Further raising of the pH to 11.7 resulted in a calcium content of 10.6 mg/mL. The precipitate was separated from the liquid, and the latter was used for calcium carbonate precipitation in accordance with Example 54, below.

EXAMPLE 28

This example describes purification of the calcium chloride solution obtained by processing of mixed office sludge in accordance with Example 1. Non-calcium salts, also extracted from the sludge, were separated by fractional precipitation with sodium carbonate followed by removal of the precipitated non-calcium salts as their insoluble carbonates and/or hydroxides. The latter are formed as a result of rising pH in the mixture due to carbonation.

30 mL and then 10 mL of a 100 g/L solution of sodium carbonate (monohydrate) was added under stirring to 250 mL of the extract (pH 1.7, 5.5% solids by weight, 14.2 mg/mL elemental calcium, 3.9% calcium chloride by weight). A dark precipitate formed. Calcium content in the initial extract, and in the supernatant after 30 mL and 40 mL (total) of sodium carbonate was added, was 14.2 mg/mL, 14.5±0.5 mg/mL, and 12.8±0.7 mg/mL, respectively. After separation of the dark precipitate by filtration, the supernatant was observed to be much clearer.

The dark precipitate was collected and dried at 105° C. Its weight was 993 mg, compared to 13.75 g of total soluble material in 250 mL of the extract (5.5% by weight), including 9.75 g calcium chloride (3.9% by weight in the extract). After combustion at 525° C., its weight reduced to 633 mg of ash, i.e., 64% of the initial weight of the precipitate. The combusted material could have been organic components and/or bound water.

The resulting clarified solution of calcium chloride (supplemented with sodium carbonate, apparently converted in situ to sodium chloride) was used for calcium carbonate precipitation in accordance with Example 51.

EXAMPLE 29

The procedure of Example 28 was repeated, but with the difference that a larger batch of the calcium chloride solution obtained in Example 1 was employed.

1.6 L of solution of sodium carbonate (monohydrate, 100 g/L) was added under stirring to 10 L of the extract (pH 1.6, 5.5% solids by weight, 14.2 mg/mL elemental calcium, 3.9% calcium chloride by weight). A gray precipitate was formed. It was filtered, 400 mL of the same solution of sodium carbonate was added to the supernatant, and the precipitate was again separated by filtration. The resulting clear supernatant was used for calcium carbonate precipitation in accordance with Example 52.

EXAMPLES 30 AND 31

The procedure of Example 29 was repeated, but with the difference that soda ash was used to perform a fractional precipitation of calcium carbonate from the calcium chloride solution obtained as described in Example 1.

(EXAMPLE 30) 20 mL, then 10 mL, and then 10 mL more of 100 g/L solution of soda ash (anhydrous, calcined) were added under stirring to 250 mL of the extract (pH 1.7, 5.5% solids by weight, 14.2 mg/mL elemental calcium, 3.9% calcium chloride by weight). A dark precipitate was formed. Table 2 shows the calcium content in the initial extract, and in the supernatant after 20 mL, 30 mL (total), and 40 mL (total) of soda ash solution were added.

TABLE 2

Fractional precipitation of calcium chloride-containing extracts (250 mL) obtained from mixed office sludge (Example 1) with soda ash, 100 g/L.

| Soda ash added, mL | pH | Elemental calcium concentration in the supernatant, mg/mL | Calcium chloride concentration in the supernatant, % |
|---|---|---|---|
| 0 | 1.7 | 14.2 | 3.9 |
| 20 | 6.6 | 14.2 | 3.9 |
| +10 | 6.6 | 12.9 | 3.6 |
| +10 (40 mL total) | 6.9 | 11.0 | 3.1 |

The resulting clarified solution of calcium chloride (supplemented with sodium carbonate, apparently converted in situ to sodium chloride) was used for calcium carbonate precipitation in accordance with Example 53.

(EXAMPLE 31) 800 mL and then 160 mL of 100 g/L solution of soda ash (anhydrous, calcined) was added under stirring to 4 L of the extract. A dark precipitate formed. Table 3 shows the calcium content in the initial extract and in the supernatant after the soda-ash solution was added.

TABLE 3

Fractional precipitation of calcium chloride-containing extracts (4 L) obtained from mixed office sludge (Example 1) with soda ash, 100 g/L.

| Soda ash added, mL | Elemental calcium concentration in the supernatant, mg/mL | Calcium chloride concentration in the supernatant, % |
|---|---|---|
| 0 | 14.2 | 3.9 |
| 800 | 9.0 | 2.5 |
| 960 | 8.1 | 2.2 |

The resulting clarified solution of calcium chloride was used for calcium carbonate precipitation in accordance with Example 54.

EXAMPLE 32

The procedure of Example 25 was repeated, but with the difference that the calcium nitrate solution obtained in Example 8 was purified from accompanying salts by raising the pH of the solution and removing the precipitated non-calcium salts as their insoluble hydroxides.

8 L of the extract obtained in Example 8, in stoichiometric proportion to the calcium carbonate content in the sludge, was employed in this Example. The solution had a pH of 1.9, and contained 7.7% (w/w) of soluble material, 73% of which was calcium nitrate. The latter figure was calculated from the elemental calcium content in the liquid extract, determined to be 13.7 mg/mL, which translates into 5.6% $CaCl_2$ in the extract by weight.

The pH of the extract was brought to 10.4 through the addition of 50% NaOH. A bulky precipitate formed in the course of titration. Overnight, the pH of the mixture increased to 11.2. The sediment was collected on a filter and dried at 105° C. It contained calcium, aluminum, magnesium and silicon (see Table 10 below). From 6-L and 570-mL batches of the extract, 67.5 g and 4.9 g, respectively, of dry precipitate was recovered (based on soluble material content, these volumes of the extract should have contained 462 g and 43.9 g of solids, respectively, 336 g and 31.9 g of which would have been calcium nitrate). Elemental calcium concentration decreased slightly, from 13.7 mg/mL in the initial extract to 13.2 mg/mL in the supernatant at pH 11.2. This corresponded to a $Ca(NO_3)_2$ concentration of 5.6% and 5.4%, respectively. Further increase of the pH to 11.6, 11.7, 11.9, and 12.0 led to calcium concentrations in the supernatant of 13.0, 13.1, 12.0, and 11.4 mg/mL, respectively.

A slightly yellowish supernatant obtained by filtration of the 6-L batch was titrated with 50% NaOH to pH 11.7, then filtered again; the resulting solution of calcium nitrate (supplemented with sodium hydroxide and sodium nitrate, formed in situ) was used for calcium carbonate precipitation in accordance with Example 60.

EXAMPLES 33 AND 34

The procedures of Examples 30 and 31 were repeated, but with the difference that the calcium nitrate solution obtained as described in Example 9 was carbonated with soda ash in order to purify calcium salts from other salts also extracted from the sludge.

(EXAMPLE 33) 40 mL of soda ash solution (100 g/L) was added in 10-mL increments under stirring to 250 mL of the extract (pH 1.6, 6.8% solids by weight, 15.36 mg/mL elemental calcium, 6.3% calcium nitrate by weight). A gray precipitate was formed. Table 4 shows the calcium content in the liquid during the course of carbonation, along with additional data concerning precipitation of calcium carbonate with soda ash.

TABLE 4

Fractional precipitation of calcium nitrate-containing extracts (250 mL) obtained from mixed office sludge (Example 9) with soda ash, 100 g/L.

| Soda ash added, mL | pH | Elemental calcium concentration in the supernatant, mg/mL | Calcium nitrate concentration in the supernatant, % |
|---|---|---|---|
| 0 | 1.6 | 15.4 | 6.3 |
| 10 | 6.4 | 14.5 | 5.9 |
| +10 | 6.4 | 12.8 | 5.2 |
| +10 | 6.5 | 11.3 | 4.6 |
| +10 (40 mL total) | 6.9 | 9.2 | 3.8 |
| 50 mL total | 7.0 | 7.7 | 3.2 |
| 120 mL total | 9.2 | 0 | 0 |
| 130 mL total | 9.6 | 0 | 0 |

(EXAMPLE 34) 2.56 L and then 1.28 L of a 100 g/L solution of soda ash was added under stirring to 16 L of the extract. A gray precipitate formed, and was discarded after separation. The calcium content in the liquid during the course of carbonation is shown in Table 5.

TABLE 5

Fractional precipitation of calcium nitrate-containing extracts (16 L) obtained from mixed office sludge (Example 9) with soda ash, 100 g/L.

| Soda ash added, L | pH | Elemental calcium concentration in the supernatant, mg/mL | Calcium nitrate concentration in the supernatant, % |
|---|---|---|---|
| 0 | 1.6 | 15.4 | 6.3 |
| 2.56 | 6.4 | 9.5 | 3.9 |
| +1.28 (3.84 L total) | 6.9 | 6.8 | 2.8 |

The resulting clarified solution of calcium nitrate was used for calcium carbonate precipitation in accordance with Example 55.

EXAMPLES 35 AND 36

The procedures of Examples 33 and 34 were repeated, but with the difference that the calcium nitrate solution was obtained as described in Example 10, and the carbonation of the liquid was performed using potassium carbonate.

(EXAMPLE 35) 20 mL, 40 mL, and 80 mL of a potassium carbonate solution (1 g/mL) were added under stirring to 100 mL of the extract (pH 3.3, 17.9% solids by weight, 16.8% calcium nitrate by weight). The pH of the liquid increased from 3.3 to 6.4, 11.7, and 12.2, respectively. A yellow precipitate was formed. The calcium content in the dried liquid decreased in the course of the carbonation from 22.9% to 6.7%, 1.0% (calcium content in the supernatant was 1.6 mg/mL, corresponding to 0.66% calcium nitrate by weight), and 0, respectively.

(EXAMPLE 36) A different 1-L batch of extract, obtained in the manner of Example 35, was used. The pH of the liquid was 2.4. 300 mL, of a 1 g/mL, solution of potassium carbonate were added in 100-ml portions to 1L of the extract.

After the first 100-mL portion of $K_2CO_3$ solution was added, a precipitate appeared immediately, the pH increased from 2.4 to 4.0, and after separating of the precipitate by centrifugation, the pH further increased to 6.0. The precipitate was collected and dried at 105° C. It contained 36.0% elemental calcium, translating into 90% of the $CaCO_3$ content in the precipitate. After combustion at 525° C. (weight loss was 6.1%), the calcium content increased to 38.1%, corresponding to 95.25% $CaCO_3$.

After the second 100-mL portion of $K_2CO_3$ solution was added to the separated supernatant, a slurry formed, reflecting a mix of white and yellow precipitates. The pH increased further to 6.6, and the liquid contained only 6.5 mg/mL elemental calcium, i.e., 2.7% calcium nitrate by weight. The precipitate was collected and dried at 105° C. It contained 35.3% elemental calcium, translating into 88% $CaCO_3$ in the precipitate. After combustion at 525° C. (weight loss was 7.1%), the calcium content increased to 37.3%, corresponding to 93.3% $CaCO_3$.

After the third 100-mL portion of $K_2CO_3$ solution was added to the separated supernatant, the pH increased to 10.4 and the liquid contained only 0.64 mg/mL of elemental calcium, i.e., 0.26% calcium nitrate by weight. The precipitate was collected and dried at 105° C. It contained 28.8% elemental calcium, translating into 72% $CaCO_3$ in the precipitate. After combustion at 525° C. (weight loss was 6.9%), the calcium content increased to 34.3%, corresponding to 85.8% $CaCO_3$.

All three batches of the precipitate were pooled, washed 5 times with water, and dried at 105° C. The total weight was 123 g. The dry precipitate contained 36.7% elemental calcium, translating into 92% $CaCO_3$ in the precipitate. When combusted at 525° C., the calcium content increased to 38.4%, i.e., to 96% $CaCO_3$ in the combusted material.

EXAMPLES 37 THROUGH 39

These examples describe fractional precipitation of calcium carbonate from calcium chloride solutions obtained by processing mixed office sludge (Example 5), and ash residues after combustion of the sludge at 525° C. (Example 6) and 900° C. (Example 7), using potassium carbonate (Examples 37, 38, and 39, respectively).

10 mL each of the calcium-containing extracts, obtained in Examples 5 through 7, were diluted to 40 mL. 3 mL of the potassium carbonate solution (0.67 mg/mL) were added, and the resulting precipitate was collected by centrifugation, dried at 105° C. and weighed, at which point the elemental calcium content was determined. The supernatant was mixed with another 3 mL of potassium carbonate solution, and the precipitate was collected, dried, and analyzed as described above. In a separate experiment, 12 mL of potassium carbonate was added into 40 mL of diluted calcium-containing extract, as described above. Table 6 shows the results of the precipitation.

TABLE 6

Precipitation of calcium-containing carbonates from calcium chloride-containing extracts obtained from mixed office sludge (Example 37) and sludge calcined at 525° C. (Example 38) and 900° C. (Example 39)

| Initial material | $K_2CO_3$ added mL | Precipitate, at 105° C. | | | Precipitate, at 525° C. | | |
|---|---|---|---|---|---|---|---|
| | | Carbonates, mg | Ca, % | $CaCO_3$ % | Weight loss, % | Ca, % | $CaCO_3$ % |
| Sludge | 3 | 264 | 35.0 | 88 | 7.8 ± 0.2 | 37.7 | 94 |
| | +3 | 289 | 34.7 | 87 | 5.1 ± 0.8 | 36.5 | 91 |
| | 12 | 1,261 | 35.3 | 88 | 5.5 | 37.4 | 94 |
| Ash, 525° C. | 3 | 661 | 32.8 | 82 | 6.1 | 32.4 | 81 |
| | +3 | 542 | 37.2 | 93 | 4.2 | 37.3 | 93 |
| | 12 | 1,359 | 33.7 | 84 | 6.6 | 34.7 | 87 |
| Ash, 900° C. | 3 | 901 | 38.4 | 96 | 1.5 | 38.0 | 95 |
| | +3 | 767 | 38.0 | 95 | 1.0 | 38.1 | 95 |
| | 12 | 1,913 | 33.4 | 84 | 8.0 | 35.8 | 90 |

The data show that the calcium carbonate content in the dried precipitate before and after its combustion at 525° C. was 88±1% and 93±2%, respectively (from sludge), 86±6% and 87±6% (from ash at 525° C.), and 92±7% and 93±3% (from ash at 900° C.). It is apparent that the precipitated calcium carbonate does not contain bound water, and its purity is in the neighborhood of 93%.

EXAMPLE 40

The procedure of Examples 37–39 was repeated, but with the difference that calcium carbonate was precipitated from the combined calcium nitrate solutions obtained in Examples 11 and 12. The mixed office sludge, combusted at 525° C., was used as the source of calcium, as described in those Examples.

Table 7 shows the results of precipitating calcium carbonate by adding potassium carbonate (0.67 mg/mL) into the calcium nitrate solution. 10 mL of the calcium-containing extract was diluted to 40 mL. 3 mL of the potassium carbonate solution was then added, precipitate was collected by centrifugation, dried at 105° C. and weighed, and the elemental calcium content was determined. The supernatant was mixed with another 3 mL of potassium carbonate solution, and the precipitate was collected, dried, and analyzed as described above. The second supernatant was mixed with 4 mL of potassium carbonate solution, and the precipitate was collected, dried, and analyzed as described above.

TABLE 7

Precipitation of calcium-containing carbonates from calcium nitrate-containing extracts obtained from mixed office sludge combusted at 525° C. in Examples 11 and 12.

| $K_2CO_3$ added, mL | Precipitate, at 105° C. | | Precipitate, at 525° C. | |
|---|---|---|---|---|
| | Ca, % | $CaCO_3$ % | Ca, % | $CaCO_3$ % |
| 3 | 25.2 | 63 | n.d. | n.d. |
| +3 | 23.8 | 60 | 33.2 | 83 |

TABLE 7-continued

Precipitation of calcium-containing carbonates from calcium nitrate-containing extracts obtained from mixed office sludge combusted at 525° C. in Examples 11 and 12.

| $K_2CO_3$ added, mL | Precipitate, at 105° C. | | Precipitate, at 525° C. | |
|---|---|---|---|---|
| | Ca, % | $CaCO_3$ % | Ca, % | $CaCO_3$ % |
| +4 | 27.7 | 69 | 35.2 | 88 |

EXAMPLE 41

The procedure of Example 40 was repeated, but with the difference that calcium carbonate was precipitated from the combined calcium acetate solutions obtained in Examples 17 and 18. The mixed office sludge, combusted at 525° C., was used as the source of calcium as described in those Examples. The data are shown in the following Table 8.

TABLE 8

Precipitation of calcium-containing carbonates from calcium acetate-containing extracts obtained from mixed office sludge combusted at 525° C. in Examples 17–18.

| $K_2CO_3$ added, mL | Precipitate, at 105° C. | | | Precipitate, at 525° C. | | |
|---|---|---|---|---|---|---|
| | Carbonates, mg | Ca, % | $CaCO_3$ % | Weight loss, % | Ca, % | $CaCO_3$ % |
| 3 | 100 | 25.5 | 64 | n.d. | 28.8 | 72 |
| +3 | 113 | 28.8 | 72 | 20.4 | 39.0 | 98 |
| +4 | 145 | 35.5 | 89 | 8.3 | 39.2 | 98 |

EXAMPLES 42 THROUGH 44

The procedure of Examples 37–39 was repeated, but with the difference that calcium carbonate was precipitated from the calcium chloride, calcium nitrate, and calcium acetate solutions obtained from industrial incineration ash in Examples 19 through 21, using potassium carbonate. The data are shown in the following Table 9.

TABLE 9

Precipitation of calcium-containing carbonates from calcium chloride-, calcium nitrate-, and calcium acetate-containing extracts obtained from industrial incineration ash (Examples 42 through 44)

| Acid | $K_2CO_3$ added, mL | Precipitate, at 105° C. | | | Precipitate, at 525° C. | | |
|---|---|---|---|---|---|---|---|
| | | Carbonates, mg | Ca, % | $CaCO_3$ % | Weight loss, % | Ca, % | $CaCO_3$ % |
| HCl | 3 | Little | n.d. | n.d. | n.d. | n.d. | n.d. |
| | +3 | 875 | 33.7 | 84 | 7.6 | 36.3 | 91 |
| | 12 | 932 | 36.4 | 91 | 7.1 | 38.2 | 98 |
| $HNO_3$ | 3 | 457 | n.d. | n.d. | n.d. | n.d. | n.d. |
| | +3 | 805 | 23.4 | 59 | 18.7 | 25.7 | 64 |
| | 12 | 1,407 | 24.0 | 60 | 17.3 | 29.0 | 73 |
| $CH_3COOH$ | 3 | 473 | 25.8 | 65 | 15.4 | 31.3 | 78 |
| | +3 | 107 | 28.2 | 71 | n.d. | n.d. | n.d. |
| | 12 | 702 | 26.5 | 66 | 12.5 | 31.1 | 78 |

It is apparent that the purest calcium carbonate was obtained from calcium chloride (up to 98% purity in the combusted material), followed by that obtained from calcium acetate (78% purity), and by that obtained from calcium nitrate (up to 73% purity).

It is also apparent that carbonates precipitated from nitrates and acetates contained significantly more combustible (at 525° C.) components compared with carbonates precipitated from chlorides. Among those combustible components can be bound water, carbonates of some other elements, etc.

EXAMPLE 45

This example describes fractional precipitation of salts, obtained by extraction of the industrial incineration ash with diluted nitric acid (Example 23), by raising the pH of the solution (through addition of sodium hydroxide in this particular case) and by removing the precipitated salts as their insoluble hydroxides or other compounds.

350 mL of the extract obtained in Example 23 was used in this Example. The solution exhibited a pH of −0.2, and contained 26.9 mg/mL of elemental calcium (corresponding to 11.0% calcium nitrate by weight).

50% NaOH was added to the extract to raise the pH. At pH 1.9 a thick gel started to form, leading to an increase in the pH to 2.6. After the gel was separated, the pH reached 2.9, and the liquid changed color from yellow-green to orange. The precipitate was collected on a filter and dried at 105° C. Its weight was 6.55 g, and it contained 6.6% elemental calcium by weight (7.6% by an independent analysis, see Table 10)—i.e., 432 mg-equivalent of calcium from 9,415 mg-equivalent in the whole extract. Hence, 4.6% of all calcium precipitated at pH 2.9. Calcium content in the supernatant decreased slightly, from 26.9 mg/mL to 25.4 mg/mL, indicating the depletion of 525 mg-equivalent of calcium, or 5.5% the total amount.

Increasing the pH in the supernatant to 9.0, with 50%, and then 4% NaOH, changed the color of the liquid to cream, and produced 7.70 g of a yellowish precipitate (dry weight). The precipitate contained 13.3% elemental calcium by weight, which was equal to 1.02 g-equivalent (from 8.89 g-equivalent of calcium in the liquid at pH 2.9). Hence, 11.5% calcium precipitated between pH 2.9 and 9.0, from a total of 16.1% of the calcium content in the initial extract. The calcium content in the supernatant decreased to 17.8 mg/mL at pH 9, corresponding to the loss of 3.2 g-equivalent of calcium, or 34% compared to the initial extract.

Further increase of the pH to 11.8 produced a white precipitate, separation of which led to a clear, colorless supernatant. The weight of the dry (at 105° C.) precipitate was 2.26 g. It contained 37.5% elemental calcium by weight, equal to 0.848 g-equivalent of calcium (from 6.23 g-equivalent of calcium at pH 9.0). Hence, 13.6% calcium precipitated between pH 9 and 11.8, from a total of 29.7% of the calcium content in the initial extract. The calcium content in the supernatant decreased to 5.0 mg/mL at pH 11.8.

The resulting solution of calcium nitrate (supplemented with sodium hydroxide and sodium nitrate, formed in situ) was used for calcium carbonate precipitation in accordance with Example 64.

EXAMPLES 46 AND 47

The procedure of Example 45 was repeated, but with the difference that fractional precipitation of salts by raising the pH of the solution (by adding sodium hydroxide to the solution) and by removing the precipitated salts was performed on the extracts obtained in Examples 22 and 24.

(EXAMPLE 46) 50% NaOH solution was added to 260 mL of the HCl-derived extract (pH 2.9, elemental calcium concentration 19.3 mg/mL, corresponding to 5.4% calcium chloride by weight) to increase the pH to 7.2. A bulky orange-colored precipitate appeared, and the elemental calcium content decreased slightly to 19.0 mg/mL. Separation of the precipitate on a filter yielded a colorless supernatant. The precipitate was dried at 105° C., and its weight was determined to be 4.51 g (compared to a total weight of calcium chloride in the liquid of 13.9 g). Analysis of the precipitate for some metals is shown in Table 10. A few drops of 50% NaOH increased the pH to 10. Further increasing the pH to 11.7 (with 4% NaOH) produced a white precipitate, and the calcium content in the liquid decreased to 17.8 mg/mL. Clear supernatant was used for calcium carbonate precipitation (see Example 65).

(EXAMPLE 47) A similar procedure was used to increase the pH of an acetic acid-derived extract (325 mL, pH 3.8, elemental calcium content 10.8 mg/mL, corresponding to 4.3% calcium acetate by weight) to 11.8. Between pH 5.5 and 7.2, the orange-colored liquid became colorless. A bulky precipitate appeared, and after its separation a clear solution was obtained. The precipitate was dried at 105° C., and its weight was determined to be 4.66 g (compared with a total weight of 13.98 g of calcium acetate in the liquid). The calcium content in the supernatant decreased to 9.2 mg/mL.

The clear liquid obtained was used for calcium carbonate precipitation in accordance with Example 66.

EXAMPLE 48

The procedure of Example 25 was repeated, but with the difference that the calcium acetate solution obtained in Example 14 was purified from accompanying salts by raising the pH of the solution and by removing the precipitated non-calcium salts as their insoluble hydroxides.

400 mL of the extract obtained by treating of the sludge with stoichiometric amount of acetic acid was used in this Example. The greenish solution exhibited a pH of 5.2, and contained elemental calcium in concentration of 17.0 mg/mL, translating into 6.7% calcium acetate in the extract by weight.

The pH of the extract was brought to 11.7 by adding 20 mL of 50% NaOH. A bulky precipitate appeared. The elemental calcium content changed only slightly, from 17.0 mg/mL in the initial extract to 16.8 mg/mL at pH 11.7. Increasing the pH to 11.84 produced a little more precipitate, but the calcium content remained at 16.8 mg/mL, corresponding to a calcium acetate concentration of 6.6%. The precipitate was collected on a filter and dried at 105° C. From 400 mL of the extract, 1.73 g of dry precipitate was recovered (based on soluble material content, this volume of the extract should have contained 36.8 g, 26.8 g of which would have been calcium acetate). The precipitate contained calcium, magnesium, and small amounts of aluminum and silicon (see Table 10).

A yellowish supernatant containing calcium acetate, obtained by filtration, was used for calcium carbonate precipitation (see Example 63).

TABLE 10

Analysis of precipitates obtained by raising pH of acid extracts of mixed office sludge or incineration ash. pH was raised by adding sodium hydroxide to extracts. The precipitates were collected and dried at 105° C., as described in Examples 25, 32, 45, 46, and 48. Analysis was performed in Galbraith Laboratories, Inc. (Knoxville, TN)

| Material | Acid | pH | Analysis, % (w/w) | | | | |
|---|---|---|---|---|---|---|---|
| | | | Ca | Al | Si | Fe | Mg |
| Sludge | HCl | 7.0 | 10.1 | 7.1 | 2.4 | 1.3 | 0.5 |
| Sludge | HCl | 11.4 | 18.8 | 3.4 | 1.0 | 0.5 | 2.5 |
| Sludge | Acetic | 11.8 | 17.8 | 0.9 | 0.8 | <0.2 | 4.1 |
| Sludge | Nitric | 11.2 | 17.2 | 2.1 | 0.6 | <0.2 | 1.4 |
| Ash | Nitric | 2.9 | 7.6 | 4.0 | 7.7 | <0.2 | 0.5 |
| Ash | HCl | 7.2 | 9.1 | 7.9 | 9.5 | <0.3 | 1.3 |

EXAMPLE 49

The procedure of Example 25 was repeated, but with the difference that the calcium acetate solution obtained in Examples 15 and 16 was purified from accompanying salts by raising the pH of the solution and by removing the precipitated non-calcium salts as their insoluble hydroxides.

400 mL of the extract obtained by combining of the extracts obtained in Examples 10 and 11 were used in this Example. The brown solution exhibited a pH of 4.6 and contained elemental calcium in concentration of 30.2 mg/mL, translating into 11.9% calcium acetate in the extract by weight.

The pH of the extract was brought to 9.6 by adding 50% NaOH. Between pH 8 and 9 the color of the liquid changed from brown to yellow, and the extract became turbid. The elemental calcium content changed only slightly, from 30.2 mg/mL in the initial extract to 29.6 mg/mL at pH 9.6. Increasing the pH to 11 produced a bulky precipitate, and the calcium content decreased to 27.4 mg/mL, which corresponded to a calcium acetate concentration of 10.8%. Further increasing the pH to 11.9 yielded a liquid whose calcium content was 27.0 mg/mL (10.7% calcium acetate by weight). The precipitate was collected on a filter and dried at 105° C. From 400 mL of the extract, 1.55 g of dry precipitate was recovered (based on soluble material content, this volume of the extract should have contained 61.6 g, of which 47.6 g would have been calcium acetate).

A yellowish supernatant obtained by filtration, containing calcium acetate (supplemented with sodium hydroxide and sodium acetate, formed in situ), was used for calcium carbonate precipitation (see Example 62).

EXAMPLE 50

The procedure of Example 48 was repeated, but with the difference that the calcium acetate solution was obtained in accordance with Example 13. It was purified from accompanying salts by raising pH of the solution and by removing the precipitated non-calcium salts as their insoluble hydroxides.

400 mL of the extract, obtained by treating of the sludge with stoichiometric amount of acetic acid, was used in this Example. The greenish solution exhibited a pH of 5.5, and contained elemental calcium in concentration of 20.2 mg/mL, translating into 8.0% calcium acetate in the extract by weight, or 83% calcium acetate content in the total solids extracted from the sludge.

The pH of the extract was brought to 11.7 by adding 50% NaOH. A bulky precipitate appeared. The elemental calcium content changed from 20.2 mg/mL in the initial extract to 18.2 mg/mL. A yellowish supernatant obtained by filtration and containing calcium acetate (supplemented with sodium hydroxide and sodium acetate, formed in situ) was used for calcium carbonate precipitation (see Example 61).

The following Examples 51–66 detail precipitation and characterization of calcium carbonate.

EXAMPLES 51 AND 52

These Examples describe precipitation of calcium carbonate from calcium chloride solutions obtained by (i) processing the mixed office sludge of Example 1, (ii) partially purifying the extract by fractional precipitation with sodium carbonate, monohydrate, and (iii) removing the precipitated accompanying salts as their carbonates and/or hydroxides as described in Example 28. Calcium carbonate was precipitated by adding a solution of sodium carbonate (monohydrate) in concentration of 100 g/L.

(EXAMPLE 51) 280 mL of a clear, practically colorless supernatant, obtained in accordance with Example 28, was used. Its elemental calcium content was 12.8 mg/mL, translating into 3.6% calcium chloride by weight. The supernatant was mixed with 10 mL of the sodium carbonate solution, and a white precipitate appeared. The liquid contained 11.6 mg/mL elemental calcium. An additional 40 mL of sodium carbonate solution were added. The concentration of elemental calcium in the liquid decreased to 5.0 mg/mL. 50 mL of sodium carbonate was then added (100 mL total). The calcium concentration dropped to 0.3 mg/mL (0.9% $CaCl_2$ by weight). At this point the white precipitate was collected by filtration, and dried at 105° C. It contained 36.9% elemental calcium by weight, corresponding to 92.3% $CaCO_3$.

(EXAMPLE 52) 11 L of a clear, practically colorless supernatant, obtained in accordance with Example 29, was treated in the same manner as in Example 51. 3.6 L of sodium carbonate (monohydrate, 100 g/L) was added to the supernatant, and 223 g of white calcium carbonate was collected and dried. It contained 38.9% elemental calcium, corresponding to $CaCO_3$ purity of 97.3%.

EXAMPLES 53 AND 54

The procedure of Examples 51 and 52 was repeated, but with the difference that soda ash was used for precipitation of calcium carbonate from calcium chloride extracts in Example 1, and partially purified in Examples 30 and 31. Calcium carbonate was precipitated by adding a solution of soda ash (100 g/L).

(EXAMPLE 53) 280 mL of a clear, practically colorless supernatant, obtained in accordance with Example 30, was used. The elemental calcium content was 11.0 mg/mL, translating into 3.1% calcium chloride by weight. The supernatant was mixed with 70 mL of the soda ash solution, and a white precipitate appeared. The pH of the liquid increased slightly from 6.9 to 7.0, and the elemental calcium content dropped from 11.0 mg/mL to 4.8 mg/mL. Further addition of 10 mL of soda ash to the liquid increased the pH to 9.1, and resulted in complete loss of calcium from the supernatant. At this point the white precipitate was collected by filtration and dried at 105° C. It contained 38.9% elemental calcium by weight, corresponding to 97.3% $CaCO_3$.

(EXAMPLE 54) 4.8 L of a clear, practically colorless supernatant, obtained in accordance with Example 31, was treated as in Example 53. It contained 8.1 mg/mL of elemental calcium, that corresponded to 2.2% calcium chloride by weight. 160 mL of the soda ash solution was added to the supernatant, a white precipitate formed, and the elemental calcium content decreased to 6.5 mg/mL (18% calcium chloride by weight). Further addition of 960 mL of the soda ash solution (1,120 mL total) lead to a calcium content in the supernatant of 0.24 mg/mL (0.7% calcium chloride by weight). 85.6 g of calcium carbonate was collected after drying of the precipitate at 105° C. It contained 38.7% elemental calcium, corresponding to $CaCO_3$ purity of 96.7%.

EXAMPLE 55

The procedure of Examples 51 and 52 was repeated, but with the difference that partially purified calcium nitrate solution was used as a source of calcium carbonate. Calcium nitrate-containing extract was obtained from the mixed office sludge of Example 9, and partially purified as in Example 34. Calcium carbonate was precipitated by adding a solution of soda ash (100 g/L).

19 L of a clear, practically colorless supernatant, obtained in accordance with Example 34, was used. The pH of the supernatant was 6.9 and the elemental calcium content was 6.8 mg/mL, translating into 2.8% calcium nitrate by weight. 4.84 L of the soda ash solution was added to the supernatant, and a white precipitate appeared. The elemental calcium content in the liquid dropped to zero. The precipitate was collected, washed with 3 L of water, and dried at 105° C. It contained 37.2% elemental calcium, corresponding to 93% $CaCO_3$.

EXAMPLES 56 THROUGH 59

These examples describe precipitation of calcium carbonate from calcium chloride solutions obtained by processing mixed office sludge in accordance with Examples 1 through 3, then partially purifying the resulting extract by raising the pH and precipitating the non-calcium salts as their hydroxides. Calcium carbonate was precipitated by adding a solution of soda ash (100 g/L) to the solutions of calcium chloride.

(EXAMPLE 56) 125 mL of a clear, practically colorless supernatant, obtained in accordance with Example 25, was employed. The pH of the solution was 11.7 and the elemental calcium content 12.2 mg/mL, translating into 3.4% calcium chloride by weight. The solution was mixed with 40 mL of the soda ash solution; white precipitate was collected, washed with water, and dried at 105° C. The precipitate contained 34.4% elemental calcium, corresponding to 86% $CaCO_3$. The filtered supernatant was mixed with 100 mL of the solution of soda ash; white precipitate was collected, washed and dried in the same manner as above. Its calcium carbonate content was 96.3%.

(EXAMPLE 57) 400 mL of the same solutions as in Example 56 were treated with soda ash in the same manner. Two batches of white precipitate, collected after 40 mL and 100 mL of the soda ash solution was added, contained 92.3% and 95.5% $CaCO_3$, respectively.

(EXAMPLE 58) 400 mL of a yellowish supernatant, obtained in Example 26, was employed. The pH of the solution was 11.7 and the elemental calcium content 11.9 mg/mL, translating into 3.3% calcium chloride by weight. The solution was mixed with 20 mL of the soda ash solution; off-white precipitate was separated and discarded, the supernatant was mixed with 20 mL of the soda ash solution, the supernatant was separated and discarded again, and the resulting supernatant was finally mixed with 110 mL of the soda ash solution. A white precipitate was collected and dried at 105° C. The precipitate contained 87% $CaCO_3$.

(EXAMPLE 59) 400 mL of a yellowish supernatant, obtained in Example 27, was employed. The pH of the solution was 11.7 and the elemental calcium content 10.6 mg/mL, translating into 2.9% calcium chloride by weight. The solution was mixed with 20 mL of the soda ash solution; a white precipitate was collected, washed with water, and dried at 105° C. The precipitate contained 34.4% elemental calcium, corresponding to 86% $CaCO_3$. The filtered supernatant was mixed again with 20 mL of the same solution of soda ash, and a white precipitate, collected and dried in the same manner, contained 87.3% $CaCO_3$. The resulting filtered supernatant was finally mixed with 110 mL of the same soda ash solution, and the collected and dried white supernatant contained 93% $CaCO_3$.

EXAMPLE 60

This example describes precipitation of calcium carbonate from the calcium nitrate solution obtained in Example 8, and then partially purified by raising the pH and precipitating non-calcium salts as their hydroxides. Calcium carbonate was precipitated by adding solution of soda ash (100 g/L) to the solutions of calcium nitrate.

400 mL of a yellowish supernatant, obtained in Example 32, was employed. The pH of the solution was 11.7 and the elemental calcium content 13.1 mg/mL, translating into 5.4% calcium nitrate by weight. The supernatant was mixed successively with 10, 20, 50, 90, 130, and 150 mL of the soda ash solution (total volumes added), and the concentration of elemental calcium in the liquid decreased from 13.1 mg/mL respectively to 10.8, 9.4, 8.6, 3.7, 1.1, and 0 mg/mL. A white precipitate was collected, washed with water, and dried at 105° C. The precipitate contained 34. 1% elemental calcium, that corresponded to 85.3% $CaCO_3$.

EXAMPLE 61 THROUGH 63

These examples describe precipitation of calcium carbonate from the calcium acetate solution obtained in accordance with Examples 13 through 16, and then partially purified by raising the pH and precipitating non-calcium salts as their hydroxides in accordance with Examples 48 through 50. Calcium carbonate was precipitated by adding solution of soda ash (100 g/L) to the solutions of calcium acetate.

(EXAMPLE 61) 400 mL of a yellowish supernatant, obtained in Example 50, was employed. The pH of the solution was 11.7 and the elemental calcium content 18.2 mg/mL, translating into 7.2% calcium acetate by weight. The solution was mixed with 20 mL of the soda ash solution; a white precipitate was collected, washed with water, and dried at 105° C. It contained 34.5% elemental calcium, corresponding to 86.3% $CaCO_3$. The filtered supernatant was mixed with again with 20 mL of the same solution of soda ash, and a white precipitate, collected and dried in the same manner, contained 88.5% $CaCO_3$. The resulting filtered supernatant was finally mixed with 110 mL of the same soda ash solution, and the collected and dried white supernatant contained 99% $CaCO_3$.

(EXAMPLE 62) 400 mL of a yellowish supernatant, obtained in accordance with Example 49, was employed. The pH of the solution was 11.9 and the elemental calcium content 27.0 mg/mL, translating into 10.7% calcium acetate by weight. The solution was mixed with 40 mL of the soda ash solution; a white precipitate was collected, washed with water, and dried at 105° C. It contained 32.4% elemental calcium, corresponding to 81% $CaCO_3$. The filtered supernatant was mixed with again with 100 mL of the same solution of soda ash, and a white precipitate, collected and dried in the same manner, contained 87.5% $CaCO_3$.

(EXAMPLE 63) 400 mL of a yellowish supernatant, obtained in accordance with Example 48, was used. The pH of the solution was 11.8 and the elemental calcium content 16.8 mg/mL, translating into 6.6% calcium acetate by weight. The solution was mixed with 40 mL of the soda ash solution; a white precipitate was collected, washed with water, and dried at 105° C. It contained 36.9% elemental calcium, corresponding to 92.3% $CaCO_3$. The filtered supernatant was mixed with again with 100 mL of the same solution of soda ash, and a white precipitate, collected and dried in the same manner, contained 95.5% $CaCO_3$.

EXAMPLES 64 THROUGH 66

These examples describe precipitation of calcium carbonate from calcium nitrate, chloride, and acetate solutions obtained in accordance with Examples 22 through 24, and then partially purified by raising the pH and precipitating non-calcium salts in accordance with Examples 45 through 47. Calcium carbonate was precipitated by adding solution of soda ash (100 g/L) to said solutions of calcium chloride.

(EXAMPLE 64) 350 mL of a clear, colorless supernatant, obtained in accordance with Example 45, was employed. The pH of the solution was 11.8 and the elemental calcium content 5.0 mg/mL, translating into 2.1% calcium nitrate by weight. The solution was mixed with 20 mL of the soda ash solution; a white precipitate was collected, washed with water, and dried at 105° C. The precipitate contained 38.8% elemental calcium, that corresponded to 97% $CaCO_3$.

(EXAMPLE 65). 250 mL of a clear, colorless supernatant, obtained in accordance with Example 46, was employed. The pH of the solution was 11.7 and the elemental calcium content 17.8 mg/mL, translating into 4.9% calcium chloride by weight. The solution was mixed with 80 mL of the soda ash solution; a white precipitate was collected, washed with water, and dried at 105° C. The precipitate contained 35.2% elemental calcium, that corresponded to 88% $CaCO_3$.

(EXAMPLE 66) 320 mL of a clear, colorless supernatant, obtained in accordance with Example 47, was employed. The pH of the solution was 11.8 and the elemental calcium content 9.2 mg/mL, translating into 3.6% calcium acetate by weight. The solution was mixed with 110 mL of the soda ash solution; a white precipitate was collected, washed with water, and dried at 105° C. The precipitate contained 34.9% elemental calcium, that corresponded to 87.3% $CaCO_3$.

It will be apparent from the above that a new and unique process has been disclosed for the recovery and purification of calcium salts from papermaking sludge. The salts recovered from sludge are suitable for many uses, including preparation of reagent chemicals, such as calcium chloride, calcium nitrate, calcium acetate, and so forth; precipitation as salts, such as calcium carbonate; preparation of liquid and solid de-icers, such as calcium acetate alone and in combination with known de-icing chemicals such as magnesium salts; preparation of sulfur-capturing sorbents based on calcium salts, etc. The invention process therefore provides new use for calcium-containing paper sludges that heretofore have primarily been burned or landfilled, creating environmental pressure. It will be clear from the present disclosure that calcium salts, and calcium carbonate in particular, resulting from waste paper sludge in general may be utilized for a wide variety of purposes.

Although this invention has been described in its preferred form and preferred practice with a certain degree of particularity, it is understood that the present disclosure of the preferred form and preferred practice has been made only by way of example and that numerous changes may be resorted to without departing from the spirit and the scope of the invention as hereinafter claimed.

What is claimed is:

1. A method of extracting calcium from an aqueous mixture comprising papermaking sludge, the mixture comprising solid and liquid phases, the method comprising the steps of:
   a. combining the mixture with an acid to solubilize substantially all calcium present in the mixture;
   b. incubating the mixture;
   c. separating a liquid fraction, the liquid fraction comprising dissolved non-calcium salts and substantially all calcium salts, and having a pH;
   d. precipitating non-calcium salts, but not the calcium salts, from the liquid fraction by raising the pH thereof; and
   e. removing the precipitate and recovering calcium salt from the liquid fraction by subsequent precipitation.

2. The method of claim 1 wherein the pH is initially acidic and is raised to at least 4.4.

3. The method of claim 1 wherein the pH is initially acidic and is raised to at least 7.0.

4. The method of claim 1 wherein the pH is raised to at least 11.5 but no more than 11.7.

5. The method of claim 1 wherein the removing step comprises adding a water-soluble acid or a water-soluble salt to form a calcium salt substantially insoluble at the resulting pH.

6. The method of claim 5 wherein a water-soluble salt is added, the salt being selected from the group consisting of carbonates, bicarbonates, borates, cinnamates, citrates, fumarates, gluconates, lactates, malates, oxalates, salicylates, succinates, sulfates, sulfites, benzoates, and arsenates.

7. The method of claim 5 wherein a water-soluble acid is added, the acid being selected from the group consisting of carbonic acid, boric acid, cinnamic acid, citric acid, fumaric acid, gluconic acid, lactic acid, malic acid, oxalic acid, salicylic acid, succinic acid, sulfuric acid, sulfurous acid, benzoic acid, and arsenic acid.

8. The method of claim 7 wherein the precipitation step comprises carbonating the mixture.

9. The method of claim 8 wherein the carbonation is accomplished by addition of a water-soluble carbonate.

10. The method of claim 8 wherein the carbonation is accomplished by addition of carbon dioxide.

11. A method of extracting calcium from an aqueous mixture comprising papermaking sludge, the mixture comprising solid and liquid phases, the method comprising the steps of:

a. combining the mixture with an acid to solubilize calcium present in the mixture;

b. incubating the mixture;

c. separating a liquid fraction, the liquid fraction comprising calcium and non-calcium salts and having a pH;

d. precipitating non-calcium salts, but not the calcium salts, from the liquid fraction by gradually carbonating it; and e. removing the precipitate; and f. continuing the carbonation to recover calcium carbonate from the liquid fraction.

12. The method of claim 11 wherein the carbonation is accomplished by addition of a water-soluble carbonate.

13. The method of claim 11 wherein the carbonation is accomplished by addition of carbon dioxide.

* * * * *